United States Patent
Haddadi et al.

(10) Patent No.: US 10,416,075 B2
(45) Date of Patent: Sep. 17, 2019

(54) METHOD FOR EVALUATING AN INDEX OF EXPOSURE OF AN EYE TO ULTRAVIOLET RADIATION AND ASSOCIATED SYSTEM

(71) Applicant: ESSILOR INTERNATIONAL (COMPAGNIE GENERALE D'OPTIQUE), Charenton-le-Pont (FR)

(72) Inventors: Ahmed Haddadi, Charenton-Lepont (FR); Melanie Tessieres, Charenton-Lepont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 0 days.

(21) Appl. No.: 15/559,712

(22) PCT Filed: Mar. 18, 2016

(86) PCT No.: PCT/EP2016/056066
§ 371 (c)(1),
(2) Date: Sep. 19, 2017

(87) PCT Pub. No.: WO2016/150885
PCT Pub. Date: Sep. 29, 2016

(65) Prior Publication Data
US 2018/0252638 A1     Sep. 6, 2018

(30) Foreign Application Priority Data
Mar. 20, 2015   (FR) ...................................... 15 52346

(51) Int. Cl.
*G01N 21/33*     (2006.01)
*G01N 21/55*     (2014.01)
*G02C 7/02*      (2006.01)

(52) U.S. Cl.
CPC ............. *G01N 21/33* (2013.01); *G01N 21/55* (2013.01); *G02C 7/027* (2013.01); *G02C 7/028* (2013.01)

(58) Field of Classification Search
CPC ........ G01N 21/33; G01N 21/55; G02C 7/027; G02C 7/028
See application file for complete search history.

(56) References Cited

U.S. PATENT DOCUMENTS 5,151,600 A * 9/1992 Black ..................... G02C 11/00
                                                      250/372
2010/0128220 A1   5/2010 Chauveau
(Continued)

FOREIGN PATENT DOCUMENTS

| EP | 2 134 249 B1 | 12/2009 |
| EP | 2 607 884 A1 | 6/2013 |
| WO | 2008/129168 A1 | 10/2008 |

OTHER PUBLICATIONS

Citek et al: "Anti-reflective coatings reflect ultraviolet radiation", Optometry—Journal of the American Optometric Association, Elsevier, NL, vol. 79, No. 3, Feb. 24, 2008 (Feb. 24, 2008), pp. 143-148, XP022496911, ISSN: 1529-1839, DOI: 10.1016/J.OPTM.2007.08. 019.
(Continued)

*Primary Examiner* — Marcus H Taningco
(74) *Attorney, Agent, or Firm* — Young & Thompson

(57) ABSTRACT

Disclosed is a method for evaluating an index of exposure to ultraviolet radiation of an eye of a wearer equipped with spectacles including at least one eyeglass, including the following steps: —determining the area of a portion of the back face of the eyeglass, which portion is directly exposed to exterior radiation when the wearer is wearing the spectacles; —determining a value representative of the exposure to ultraviolet radiation of at least one environment fre-
(Continued)

quented by the wearer; and —determining the index of exposure depending on the determined area and the determined value. An associated system is also described.

15 Claims, 2 Drawing Sheets

(56) References Cited

U.S. PATENT DOCUMENTS

2010/0195045 A1 8/2010 Nauche et al.
2013/0341523 A1* 12/2013 Citek .................. G02C 7/028
 250/372

OTHER PUBLICATIONS

Citek K: "The Eye and Solar Ultraviolet Radiation, roundtable-UV 201, Moderator: Karl Citek", Internet Citation, Jun. 18, 2011 (Jun. 18, 2011), pp. 1-19, XP002676432, Retrieved from the Internet <URL:http://www.espf.com/wp-content/uploads/2012/04/The-eye-and-solar-ultraviolet-radiation-Karl-Citek-roundtable-UV-2011-Karl-Citek.pdf> [retrieved on May 23, 2012].
Jean Krutmann et al: "Towards standardization of UV eye protection: what can be learned from photodermatology?", Photodermatology, Photoimmunology & Photomedicine, vol. 30, No. 2-3, Dec. 5, 2013 (Dec. 5, 2013), pp. 128-136, XP055143426, ISSN: 0905-4383, DOI: 10.1111/phpp.12089.
Essilor International: "The Eye-Sun Protection Factor (E-SPF): A New Way to Look at Ultraviolet Radiation Hazard and Eye Protection", Internet Citation, Jan. 1, 2012 (Jan. 1, 2012), pp. 1, XP002676423, Retrieved from the Internet <URL:http://www.espf.com/wp-content/uploads/2012/04/E-SPF-A-new-way-to-look-at-ultraviolet-radiation-hazard-and-eye-protection.pdf> [retrieved on May 22, 2012].
Essilor International: "Maximizing Protection from Ultraviolet Radiation, Hazards: Assessing the Risks; Finding Solutions", Internet Citation, Apr. 30, 2012 (Apr. 30, 2012), pp. 1-4, XP002676425, Retrieved from the Internet <URL:http://www.espf.com/wp-content/uploads/2012/04/Maximizing-Protection-from-Ultraviolet-Radiation-Hazards-Assessing-the-Risks-Finding-Solutions.pdf> [retrieved on May 23, 2012].
Francine Behar-Cohen et al: "Ultraviolet damage to the eye revisited: eye-sun protection factor (E-SPF), a new ultraviolet protection label for eyewear", Clinical Ophthalmology, Dec. 1, 2013 (Dec. 1, 2013), pp. 87, XP055143427, DOI: 10.2147/OPTH.S46189.
Sakamoto Y et al: "[Effectiveness of eyeglasses for protection against ultraviolet rays]", Nihon Ganka Gakkai Zasshi—Journal of Japanese Ophthalmological Society—ACTA Societatis Ophthalmologicae Japonicae, Tokyo, JP, vol. 103, No. 5, May 1, 1999 (May 1, 1999), pp. 379-385, XP009159642, ISSN: 0029-0203.
International Search Report, dated Jun. 22, 2016, from corresponding PCT/EP2016/056066 application.

* cited by examiner

METHOD FOR EVALUATING AN INDEX OF EXPOSURE OF AN EYE TO ULTRAVIOLET RADIATION AND ASSOCIATED SYSTEM

TECHNICAL FIELD TO WHICH THE INVENTION RELATES

The present invention relates to the protection of the eyes from ultraviolet radiation.

It more particularly relates to a method for evaluating an index of exposure of an eye to ultraviolet radiation and to an associated system.

TECHNOLOGICAL BACKGROUND

As explained in document EP 2 607 884, when it is sought to protect the eyes of a wearer from ultraviolet radiation by means of spectacles, it is necessary to take into account not only radiation transmitted through the eyeglasses of these spectacles, but also rays reflected from the back face of these eyeglasses.

In this logic, the aforementioned document proposes to calculate an ESPF index that quantifies the overall reduction of ultraviolet radiation achieved by the spectacles in question and combines to do this a value of transmission through the spectacles and a value of reflection from the back face of the spectacles.

The ESPF index thus calculated makes an objective approach to evaluation of the protection from ultraviolet radiation provided by various spectacles possible.

In contrast, the protective needs of users are often poorly evaluated, in particular as regards the ultraviolet radiation reflected from the back face of eyeglasses. This is because this effect, which is not easily understandable by nonspecialists, is difficult to quantify, whereas a specific treatment of the back face of eyeglasses is necessary to prevent it.

SUBJECT OF THE INVENTION

In this context, the present invention provides a method for evaluating an index of exposure to ultraviolet radiation of an eye of a wearer equipped with spectacles comprising at least one eyeglass, comprising the following steps:
  determining the area of a portion of the back face of said eyeglass, which portion is directly exposed to exterior radiation when said wearer is wearing said spectacles;
  determining a value representative of the exposure to ultraviolet radiation of at least one environment frequented by the wearer; and
  determining the index of exposure depending on the determined area and the determined value.

Thus, an index of exposure that represents concisely the amount of ultraviolet radiation that a given wearer risks receiving over the long term when he wears the aforementioned spectacles in the indicated environment(s) is obtained.

According to optional and therefore nonlimiting features:
  the step of determining said area comprises a step of calculating said area depending on morpho-geometric parameter values of the wearer and of the frame;
  the method comprises a step of measuring at least one of said morpho-geometric parameter values;
  the method comprises a step of determining at least one of said morpho-geometric parameter values from an image of the wearer wearing said spectacles;
  the method comprises a step of inputting at least one of said morpho-geometric parameter values on a user interface;
  the step of determining said area comprises a step of evaluating said area from an image taken while the wearer is illuminated, for example by an optionally coloured light (in the domain of the visible) or as a variant by another sort of radiation such as ultraviolet radiation;
  said value representative of the exposure is determined depending on at least one piece of information input on a user interface;
  the index of exposure is determined by multiplying the determined value representative of the exposure by a coefficient dependent on the determined area.

The invention also provides a system for evaluating an index of exposure to ultraviolet radiation of an eye of a wearer equipped with spectacles comprising at least one eyeglass, comprising:
  a module for determining the area of a portion of the back face of said eyeglass, which portion is directly exposed to exterior radiation when said wearer is wearing said spectacles;
  a module for determining a value representative of the exposure to ultraviolet radiation of at least one environment frequented by the wearer; and
  a module for determining the index of exposure depending on the determined area and the determined value.

According to optional and therefore nonlimiting features:
  the module for determining said area is designed to calculate said area depending on morpho-geometric parameter values of the wearer and of the frame;
  the system comprises a device for measuring at least one of said morpho-geometric parameter values, the measuring device optionally including an image sensor;
  the system comprises a module for determining at least one of said morpho-geometric parameter values from an image of the wearer wearing said spectacles;
  the system comprises a tool for inputting (for example a touchscreen or, as a variant, a keyboard or a mouse) at least one of the morpho-geometric parameter values on a user interface (typically displayed on a screen of the system);
  the system comprises a projector suitable for illuminating the wearer (for example with a coloured light) and an image-capturing apparatus suitable for taking an image of the wearer;
  the module for determining said area is designed to evaluate said area from said image;
  the system comprises a tool for inputting a piece of information on a user interface;
  the module for determining said value representative of the exposure is designed to determine said value representative of the exposure depending on said piece of information;
  the module for determining the index of exposure is designed to determine the index of exposure by multiplying the determined value representative of the exposure by a coefficient dependent on the determined area.

Such a system may comprise one or more electronic devices, based for example on a microprocessor-based architecture. In this case, the aforementioned modules may be formed by a hardware component of the electronic device in question and/or by the association of the aforementioned microprocessor, of a memory and program instructions (optionally stored in this memory) allowing, when these instructions are executed by the aforementioned microprocessor, the implementation of at least one functionality of the module in question (including for example the processing of data stored in the aforementioned memory).

DETAILED DESCRIPTION OF AN EXEMPLARY EMBODIMENT

The description which follows with reference to the appended drawings, which are given by way of nonlimiting examples, will make it easy to understand the essence of the invention and how it can be achieved.

A wearer P wears on his head T a pair of spectacles comprising a frame M and two eyeglasses V located in line with his left eye OG and his right eye OD, respectively.

Each eyeglass V has a back face AR turned towards the eye in question OG, OD and a front face AV turned toward the gaze direction R of the wearer P.

Here the gaze direction R is considered to be the horizontal primary gaze axis that the wearer P adopts when he is gazing straight ahead and that is therefore parallel to the sagittal plane PS of the wearer P.

The eyeglasses V may be tinted, for example by means of pigments, dyes or absorbers, in order to filter some of the light rays, such as is the case for spectacles providing solar protection. As a variant, the eyeglasses V may be colourless.

These eyeglasses V may moreover be ophthalmic lenses for correcting an ametropia of the wearer P. The eyeglasses V may in contrast have no optical effect, as in the case of spectacles providing solar protection but no correction.

The eyeglasses V are typically made of organic glass, for example of a thermoplastic or thermoset such as polycarbonate.

Generally, the substrate of an eyeglass V may be any substrate widely used in the optical field, and in particular in the field of ophthalmic optics.

The thermoplastic may for example be chosen from: the polyamides, the polyimides, the polysulfones, the polycarbonates, polyethylene terephthalate, polymethyl methacrylate (PMMA), and the associated copolymers.

The thermoset plastic may for example be chosen from: cyclo-olefin copolymers such as ethylene/norbornene or ethylene/cyclopentadiene copolymers, (co)polymers of allyl carbonates of polyols, such as diethyleneglycol bis(allyl carbonate) (for example sold under the trade name CR39® by PPG Industries, having a refractive index of 1.5), (co)polymers of (meth)acrylic acid and the associated esters, which may be derivatives of bisphenol A, (co)polymers of thio(meth)acrylic acid, (co)polymers of allylic acid, which may be derivatives of bisphenol A, phthalic acid and allylic aromatic compounds such as styrene, (co)polymers of urethane and thio-urethane, epoxy (co)polymers and (co)polymers of sulphide, bisulphide, episulphide, and their combinations.

It is especially possible to use allylic and (meth)acrylic copolymers having a refractive index comprised between 1.54 and 1.58, or a polyurethane (such as those of the MR series sold by Mitsui chemicals: MR6®, MR7®, MR8®, MR100, MR174®).

The term "(co)polymer" is understood to mean a copolymer or a (homo)polymer. The term "(meth)acrylate" is understood to mean an acrylate or a methacrylate. The term "polycarbonate (PC)" is understood to mean both homopolycarbonates and copolycarbonates and sequenced copolycarbonates.

The substrates may be obtained by polymerization of blends of the above monomers, or may even comprise blends of these polymers and (co)polymers.

Figure 1:
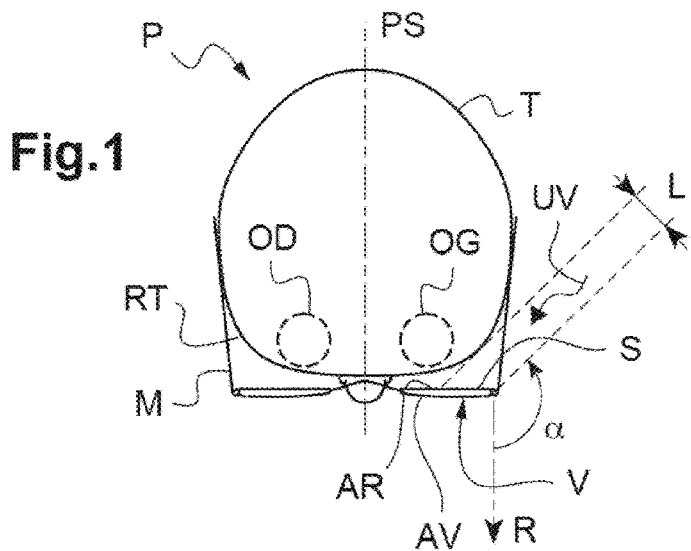
FIG. 1 is a schematic representation of the context in which the phenomenon of reflection from the back face of spectacle eyeglasses occurs.

For the sake of simplicity, FIG. 1 shows spectacles the eyeglasses V of which are perpendicular to the gaze direction R of the wearer P. Each eyeglass V could however be slightly inclined in order to make a non-zero face-form angle to the (vertical) plane perpendicular to the gaze direction R of the wearer.

As illustrated in FIG. 1, some of the ambient ultraviolet radiation UV is incident on the back face AR of each eyeglass V because of the free space present between this back face AR and the temporal region RT of the head T of the wearer P.

Specifically, one portion of the area S of the back face AR of a given eyeglass V is exposed to incident UV rays coming from a direction making an angle $\alpha$ to the gaze direction R, with $\alpha$ comprised between 90° and 180° ($\alpha$=135° in FIG. 1).

As may be seen in FIG. 1, for a given angle $\alpha$ this exposed portion of the area S corresponds to an incident beam the width L of which depends on the shape of the temporal region RT of the wearer P and on the geometry of the eyeglass V (or, equivalently, of the frame M that holds this eyeglass V).

In the absence of a specific treatment of the back face AR, these incident UV rays are to a large extent reflected by the back face AR, then propagate, in a large part, in the direction of the eye OD, OG in question, this possibly being harmful to the wearer P when this phenomenon is repeated.

The invention aims exactly to quantify this risk.

Figure 2:
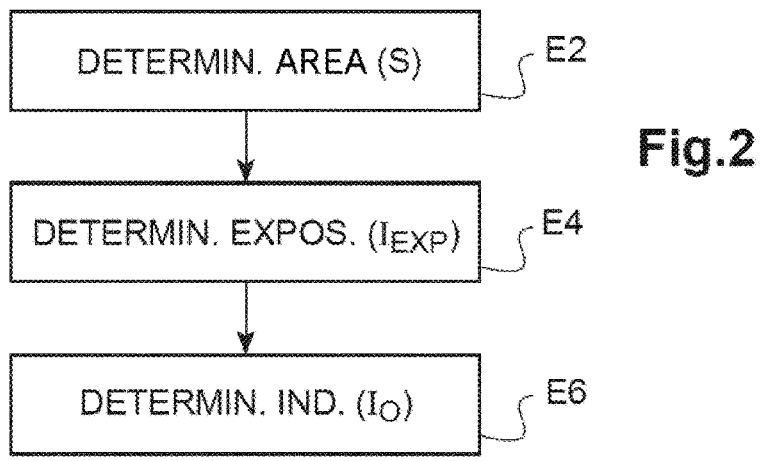
FIG. 2 shows the main steps of a method for evaluating an index of exposure of an eye to ultraviolet radiation according to the invention.

FIG. 2 shows the main steps of a method for evaluating an index of exposure of an eye to ultraviolet radiation according to the invention.

This method is for example implemented by an electronic apparatus, such as a microprocessor-based programmable electronic apparatus, in which case the steps mentioned below are implemented because of the execution, by the microprocessor of the programmable electronic apparatus, of computer program instructions stored in a memory of the programmable electronic apparatus.

As a variant, this method may be implemented in a system comprising a plurality of such electronic apparatuses, in which case each step of the method is carried out by one of said electronic apparatuses.

Examples of such systems are given in the embodiments described below with reference to FIGS. 3 to 6.

The method starts with a step E2 of determining the area S of the portion of the back face AR of the eyeglass V directly exposed to exterior UV radiation when said wearer P wears the spectacles equipped with this eyeglass V.

For example, the exterior UV radiation is considered to be transmitted in a particular direction (in projection in a horizontal planning), here the direction making an angle α=135° to the gaze direction R, as shown in FIG. 1.

As indicated above, this area S depends on the morphology of the wearer P (in particular the morphology of his temporal region RT) and on the shape of the spectacles (i.e. the geometry of the eyeglass V and/or the frame M).

As will become more clearly apparent from the examples given below, the step E2 does not necessarily however require the wearer P to actually be wearing the spectacles in question (the area S possibly for example being determined by simulation).

The method also comprises a step E4 of determining a value $I_{EXP}$ representative of the exposure to ultraviolet radiation of one or more environments frequented by the wearer P.

In the example in FIG. 2, this step E4 is carried out after the step E2 described above. As a variant, the step E4 could however be carried out before the step E2.

The step E4 is for example carried out by means of a user interface of an electronic apparatus (such as those mentioned above) and comprises a substep of inputting (carried out by the wearer P or another person, for example an optician) via this user interface pieces of information descriptive of the environments frequented by the wearer P.

These pieces of information descriptive of the environments frequented by the wearer P may be geographic positions at which the wearer P is regularly found (geographic position of his place of residence, geographic position(s) frequented while travelling, for example geographic position(s) of one or more holiday destinations) and/or characteristics of journeys carried out by the wearer P (frequency and duration).

According to other embodiments, these pieces of information descriptive of the environments frequented by the wearer P may be associated with activities practised by the wearer P (pieces of information indicative of the practice of a nautical sport corresponding to a marine environment, pieces of information indicative of the practice of a snow sport corresponding to a snowy environment, etc.).

Step E4 furthermore comprises a sub-step of determining said value $I_{EXP}$ representative of the exposure, depending on the aforementioned descriptive pieces of information and on average exposure data associated with the frequented environments.

To do this, an electronic device (such as the electronic device equipped with the aforementioned user interface) stores (or has access via a communications network to) average exposure data associated with a large number of possible environments. These average exposure data are for example statistical ultraviolet-radiation exposure data for various places in a region, country, or one or more continents.

This electronic device then for example proceeds as follows to determine the value $I_{EXP}$ representative of the exposure:
  it determines an average value of the exposure of the wearer P by calculating a weighted mean of the various average exposure data associated with the environments frequented by the wearer P, by weighting each average exposure datum by a coefficient obtained from the pieces of information descriptive of the environments frequented by the wearer P; and
  it determines the value $I_{EXP}$ representative of the long-term exposure of the wearer P depending on the aforementioned exposure value, for example on a scale varying between 1 and 3 (corresponding to an exposure value comprised between 20 W/m² and 60 W/m², respectively).

The method of FIG. 2 lastly comprises a step E6 of determining the sought exposure index depending on the area S determined in the step E2 and the value $I_{EXP}$ determined in the step E4 and representative of the long-term exposure of the wearer P to ultraviolet radiation.

This step E6 is for example implemented by an electronic device such as one of the aforementioned devices and may comprise the following sub-steps:
  determining a coefficient $I_S$ representative of the area S, the coefficient $I_S$ for example varying between 1 and 5 when the area S varies between 150 mm² and 750 mm²;
  determining the index $I_O$ of exposure of the eye by multiplying the value $I_{EXP}$ representative of the exposure to ultraviolet radiation by the coefficient $I_S$ representative of the area S.

Such an index $I_O$ of exposure of the eye therefore varies between 1 and 15 and makes it possible to apprehend very simply the quantity of ultraviolet rays reflected toward the eye OG, OD from the back face AR of the eyeglass V and the need to treat this back face AR, for example by depositing a coating that is antireflective in the ultraviolet.

Figure 3:
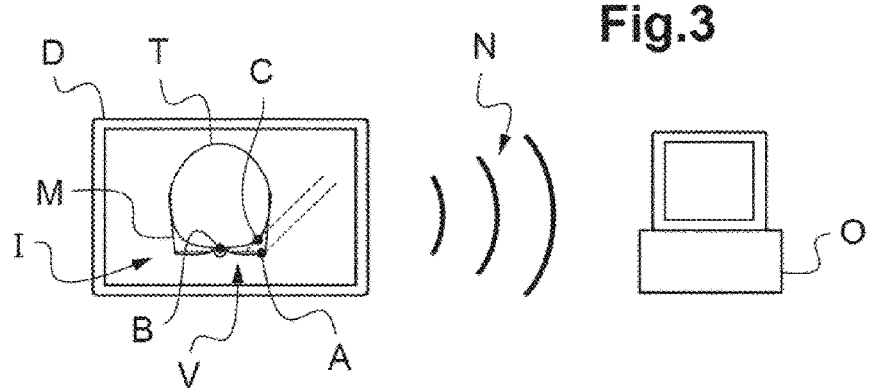
FIG. 3 shows a first exemplary system for determining the area of the back face directly exposed to exterior radiation.

FIG. 3 shows a first exemplary system for determining the area S of the back face AR directly exposed to exterior radiation.

In this example, an electronic device D equipped with an image sensor (not shown) is placed facing the head T of the wearer P in order to take an image I showing the wearer P wearing the spectacles, in an orientation allowing an image I of the same type as FIG. 1 to be obtained.

The electronic device D is for example a digital tablet. As a variant, the electronic device D could be a personal computer equipped with a webcam (in which case the wearer P inclines his head in the direction of the webcam while the image I is taken in order to obtain an image I of the same type as FIG. 1).

In these two cases especially, the electronic device D may implement the capture of the aforementioned image I and the processing described below because of the execution of a dedicated program (or application) by a microprocessor of the electronic device D.

The electronic device D then determines characteristic points (here three characteristic points A, B, C) allowing the width L of the beam incident in a given direction (making an angle α to the gaze direction R, here α=135°) in the free space present between this back face AR and the temporal region RT of the head T of the wearer P to be evaluated.

These characteristic points A, B, C are here determined by a user (such as the wearer P himself or an optician) who inputs them on a user interface of the electronic device D, the characteristic points A, B, C for example being identified by the user in the image I (here by pressing on the touchscreen of the aforementioned digital tablet level with the characteristic points). As a variant, these characteristic points A, B, C could be obtained by the recognition of shapes in the image I.

As already indicated, in the example described here three characteristic points are used:
  a point A located at the lateral end of the eyeglass V, from which end the temple of the frame M extends;
  a point B located at the centre of the frame (between the rims of the frame, each of which is equipped with an eyeglass V); and a point C located in the temporal region RT, in line with the point A in a direction perpendicular to the aforementioned incident beam.

To make it easier for the user to input these characteristic points, the electronic device D may for example display (on its touchscreen), in superposition on the image I, sections drawn from each of the points A and C in the preset direction of the incident beam, and allow the user to move the characteristic point C especially (over the touchscreen) until the section drawn from the point C is tangent to the temporal region RT.

The electronic device D may moreover exchange data with a computer O via a computer network N. In the example shown in FIG. 3, the computer O is a personal computer (equipping for example the shop of an optician) and the computer network N is a local wireless network (or WLAN for wireless local area network). As a variant, especially in the case where the electronic device D is a personal computer, the computer network N is for example the Internet and the computer O a remote server.

According to one first possible embodiment, the electronic device D determines the width L of the aforementioned beam from the positions of the characteristic points A, B, C possibly using complementary data stored in the computer O (and transmitted to the electronic device D via the network N).

According to a second possible embodiment, the electronic device D transmits to the computer O the positions of the characteristic points A, B, C, and the computer O determines the width L of the aforementioned beam from the positions of the characteristic points A, B, C, possibly using complementary data stored in the computer O.

In both cases, it is possible to make provision, for example, for the computer O to store (by way of complementary data, for example in association with an identifier of the wearer P) the dimensions of the frame M, and especially the width of the frame $I_M$, in which case the width L of the beam may be determined by proportionality between the distances in the image I and the actual distances, for example using the formula:

$$L = AC \cdot (0.5 \cdot I_M)/AB.$$

As a variant, a graduated rule could be positioned, during the capture of the image I, in proximity to the frame M in order to allow the width L of the beam to be determined by comparison of the distance AC (in the image I) with the graduations of the graduated rule observed in the image I.

The electronic device D (or the computer O) may then calculate the sought area S depending on the width L just determined, for example using the following formula:

$$S = L \cdot h_{MOY}/\cos(180° - \alpha + \Delta),$$

where $h_{MOY}$ is the average height (or level) of the eyeglass V and $\Delta$ is a dihedral angle associated with the face-form angle of the frame M (the face-form angle of the frame corresponding to the angle of the dihedral formed by the mean planes of the two rims of the frame, as explained for example in patent application WO 2008/129 168). It will be recalled, as indicated above, that in the example described here a value $\alpha=135°$ is used.

According to one possible embodiment, the average height $h_{MOY}$ of the eyeglass V and/or the dihedral angle $\Delta$ are stored among the aforementioned complementary data, in association with an identifier of the wearer P and the width $I_M$ of the frame M of the spectacles worn by the wearer P.

According to another possible embodiment, the average height $h_{MOY}$ and/or the dihedral angle $\Delta$ may be determined by taking a face-on image of the wearer P wearing the spectacles and estimating the average height $h_{MOY}$ (and the dihedral angle $\Delta$) on the basis of this image (for example using a method of the same type as one of those described above for determining the width L of the incident beam).

According to these two possible embodiments, the average height $h_{MOY}$ may be limited (bounded) by a given predetermined value, for example comprised between 40 mm and 45 mm, before application in the calculation of the area S in the formula given above (the ultraviolet rays reflected not reaching the sensitive zone of the eye for larger eyeglass heights).

According to yet another possible embodiment, it is possible to use a fixed predetermined average height $h_{MOY}$ (typically comprised between 30 mm and 40 mm, for example 35 mm). Likewise, in a simplified approach, it is possible to use a dihedral angle $\Delta$ of zero.

For more precision, it is also possible to apply to the average heights (determined as was just suggested) a form factor, based for example on a classification of the spectacles worn by the wearer P into one or more categories associated each with a specific form factor.

The area S determined as described above may then be used in the step E6 described above. In this case, the electronic device D (or, as a variant, the computer O) may implement the step E4 described above and/or the step E6 described above.

Figure 4:
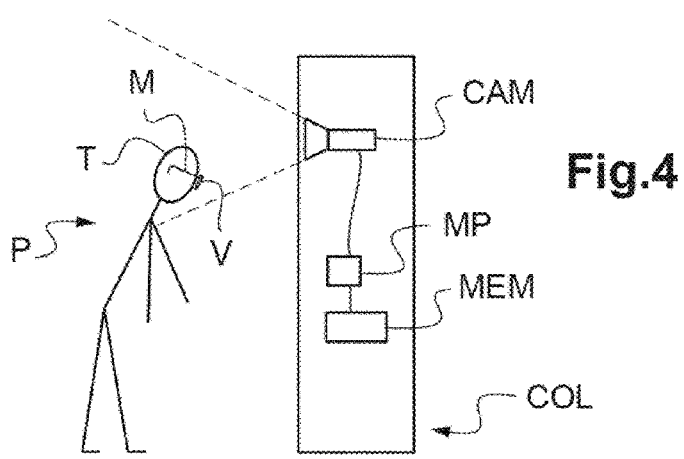
FIG. 4 shows a second example of such a system.

FIG. 4 shows a second exemplary system for determining the area S of the back face AR directly exposed to exterior radiation.

In this second example, the system for determining the area S takes the form of a column COL equipped with an image-capturing apparatus CAM and that thus forms a system for measuring various morpho-geometric parameters of the wearer P (and possibly of the frame M). Such a measuring apparatus is for example described in document EP 2 134 249.

The column COL comprises a microprocessor MP and a memory MEM. The column COL may possibly furthermore comprise a communications module (not shown) in order to allow the microprocessor MP to exchange data with another electronic device via a computer network.

Because of the execution by the microprocessor MP of program instructions (stored for example in the memory MEM), the microprocessor MP carries out the processing described below.

The wearer P places himself in front of the column COL, in front of the image-capturing apparatus CAM, while inclining himself in the direction of the column COL so that the image-capturing apparatus CAM can take an image of the head T of the wearer P of the same type as the image I described above with reference to FIG. 3 (i.e. comparable to the representation given in FIG. 1).

According to a first embodiment, the processing carried out by the microprocessor MP on the image taken to obtain the beam width L and then the sought area S is identical to the processing described above with reference to FIG. 3 (processing carried out by the electronic device D and/or by the computer O). In this case, the column COL may comprise a touchscreen (not shown) allowing a user to input characteristic points in the image taken; as a variant, the image taken is transmitted (by means of the aforementioned communications module) to another electronic device, equipped with a touchscreen allowing characteristic points of the image taken to be input.

According to a second possible embodiment, the microprocessor MP extracts from the image taken by the image-capturing apparatus CAM pieces of information descriptive of the morphology of the head T of the wearer P and in particular of the temporal region RT.

The column COL moreover stores in the memory MEM data descriptive of the geometry of the frame M. These data descriptive of the geometry of the frame M will have for example been determined by the microprocessor MP by analysis of other images taken by the image-capturing apparatus CAM. As a variant, these data descriptive of the geometry of the frame M may be received (via the communications module) from a remote server storing, in a database, such data descriptive of geometry for many frames. (It will be noted that, in the latter case, the wearer P is not necessarily wearing the spectacles when he positions himself in front of the column COL as shown in FIG. 4).

On the basis of the pieces of information descriptive of the temporal region RT and of the pieces of information descriptive of the geometry of the frame M, the microprocessor MP may determine the width L of the free space present (in a given direction) between the temporal region RT and the back face AR of the eyeglass V held by this frame M, i.e. the width L of the incident beam in this free space (with an orientation perpendicular to the aforementioned given direction).

The microprocessor MP may then calculate the area S of the portion of the back face AR exposed to this incident beam, for example on the basis of the formula given above in the context of the description of FIG. 3, the average height $h_{MOY}$ of the eyeglass V and the dihedral angle $\Delta$ for example making up part of the data descriptive of the geometry of the frame M, which data are stored in the memory MEM as indicated above.

The microprocessor MP may then for example transmit the area S thus calculated to another electronic device, for example a personal computer equipping the shop of an optician (such as the computer O mentioned above in the context of the description of FIG. 3), in order for this other electronic device to implement the steps E4 and E6 described above.

Figure 5:
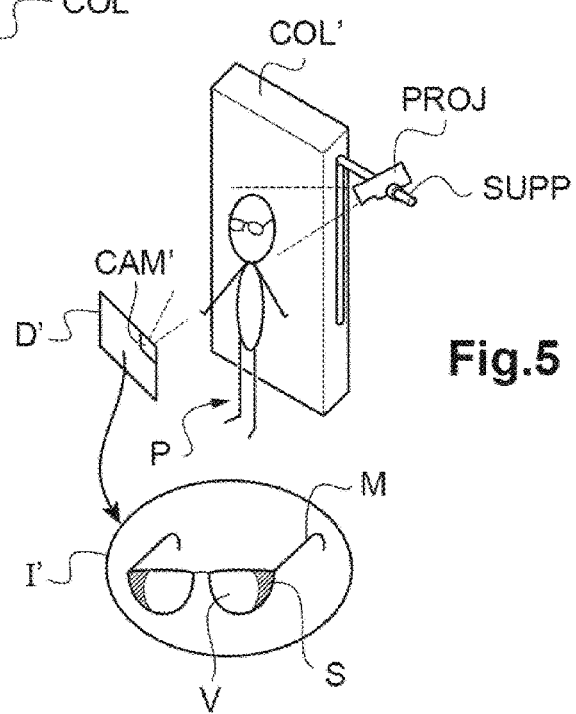
FIG. 5 shows a third example of such a system.

FIG. 5 shows a third exemplary system for determining the area S of the back face AR directly exposed to exterior radiation.

In this example, the system comprises a column COL' equipped with a, here horizontal, supporting rod SUPP that is translationally movable vertically, which extends from a side wall of the column COL', and on which is mounted a projector PROJ, for example by means of a fastener that is clip-fastenable to the supporting rod SUPP. Provision may furthermore be made for the projector PROJ to be orientable relative to the supporting rod SUPP.

The projector PROJ emits radiation, here coloured light (in the domain of the visible), that is directed toward the wearer P, who positions himself with his back to the column COL', as may be clearly seen in FIG. 5. As a variant, the projector PROJ could emit ultraviolet radiation, in which case provision will possibly be made to equip the people present with protective devices (for example specific spectacles). (It will be understood that the projector PROJ comprises a lamp suitable for generating the radiation emitted by the projector PROJ, in the ultraviolet or in the visible).

The projector PROJ therefore illuminates the wearer P from behind, in an orientation of the same type as that shown in FIG. 1, and therefore illuminates a portion of the back face AR of at least one eyeglass V of the spectacles worn by the wearer P. It will be recalled that the system described here aims to determine the area S of this illuminated portion of the back face AR. It will be noted that positioning the supporting rod SUPP (and therefore the projector PROJ) at a height larger than the height of the wearer P allows the wearer P to be illuminated from above, as would in general sunlight, which is the main source of ultraviolet radiation from which it is sought to obtain protection. Thus real situations in which reflection from the back face AR of the eyeglasses V is harmful over the long-term are simulated.

In certain cases, in particular when ultraviolet radiation is used, the spectacles of the wearer P are equipped with a means for revealing the (for example ultraviolet) radiation received. This revealing means is appended to the back face AR of at least one eyeglass V of the spectacles of the wearer P, while being borne either by the eyeglass V itself, or by the frame M. The revealing means is for example a frosted patch or a photosensitive varnish. Such a revealing means may optionally be omitted in the case described here where the projector PROJ emits optionally coloured visible light.

The system shown in FIG. 5 also comprises an electronic device D' (for example a digital tablet) including an image sensor CAM'.

An operator (for example an optician) may then use the electronic device D' to take an image I' of the spectacles worn by the wearer P, who is located with his back to the column COL', the back face AR of at least one eyeglass V of the spectacles being, as a result, illuminated by the radiation emitted by the projector PROJ.

Thus, an image I' of the spectacles is obtained, in which image clearly appears (in transparency through the eyeglasses V of the spectacles) the illuminated portion (having an area S) of the back face AR, i.e. the portion exposed to the radiation coming from the projector PROJ, in the direction determined by the relative position of the protector PROJ and the column COL' (the wearer P placing himself in a predefined position relative to the column COL').

It will be noted that the nonexposed portion of the back face AR corresponds to rays (here in the domain of the visible, for example rays of coloured light) interrupted by the head of the wearer P, as may be clearly seen in FIG. 1.

The electronic device D' (or any other electronic device to which the image I' is transmitted by communicating means not shown in FIG. 5) may then determine the area S of the illuminated portion by processing the image I'.

According to a first possibility, similar to that described above with reference to FIG. 3, the operator could identify, in the image I', characteristic points of the illuminated portion (for example using a touchscreen of the electronic device D') and the electronic device in question could determine the area S depending on the identified characteristic points.

According to a second possibility, the device in question could determine the area S of the illuminated portion by recognition of shapes in the image I'.

In both cases, the area S of the illuminated portion may be determined by comparison to the dimensions of the frame M (when these dimensions are stored by the electronic device in question or accessible to this device, for example by communication with a server storing the dimensions of many frames) or by comparison to a graduated rule mounted for example on the frame M during the capture of the image I'.

Figure 6:
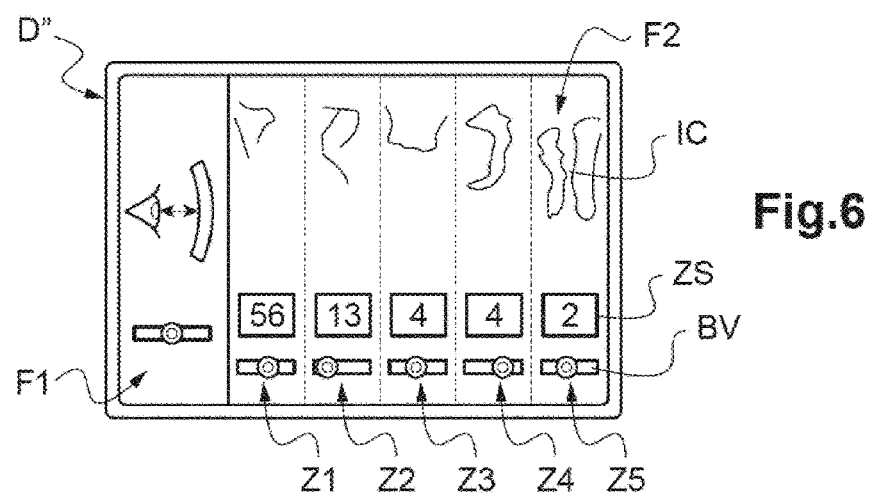
FIG. 6 shows a fourth example of such a system.

FIG. 6 shows a fourth exemplary system for determining the area S of the back face AR directly exposed to exterior radiation.

In this example, an electronic device D'' displays on a screen a user interface comprising a first window F1 and a second window F2.

The electronic device D" comprises a microprocessor and a memory. The processing described here, in particular the display of the user interface and the interaction with a user via this user interface, is carried out because of the execution by the microprocessor of the electronic device D" of instructions of a computer program (or an application) stored in the memory of the electronic device D".

The electronic device D" is for example a digital tablet and the screen may then be a touchscreen. As a variant, the electronic device D" could be a personal computer; inputting means (such as a mouse and a keyboard) are in this case provided in order for a user to be able to interact with the electronic device D" via the user interface.

The second window F2 is divided into a plurality of zones (here five zones Z1, Z2, Z3, Z4, Z5) each including an icon IC (selectable by the user), a zone ZS for inputting a numerical value and a virtual button BV (actuatable by the user).

Each zone Z1, Z2, Z3, Z4, Z5 allows the user to input a parameter used (as explained below) to determine the area S of the exposed portion of the back face AR and/or the index $I_O$ of exposure of the eye to ultraviolet radiation.

To input a given parameter, the user may input the value of the parameter in question in the inputting zone ZS of the zone Zi associated with the parameter in question, or act (via the touchscreen in the case where the electronic device D" is a digital tablet, or via the mouse in the case where the electronic device D" is a personal computer) on the virtual button BV of this zone Zi (the numerical value displayed in the corresponding inputting zone ZS then being updated in real-time depending on the position of the virtual button BV).

The user may also select the icon IC of a zone Zi associated with a given parameter, this causing a representation of the parameter in question and an additional virtual button to appear in the first window: by action of the user on this additional virtual button (by means of a touchscreen or a mouse as indicated above), the current value of the parameter is modified, this furthermore leading to a modification of the representation of the parameter in order for the current value to be visually represented; likewise, the new current value is displayed in the inputting zone ZS of the zone Zi associated with the parameter in question and the virtual button BV of the same zone Zi is moved as a consequence.

In the example described here:
the first zone Z1 allows the eyeglass-eye distance DVO (associated with the frame M and the wearer P) to be input;
the second zone Z2 allows a parameter representative of the geometry of the eyeglass V (such as the "base eyeglass" parameter mentioned in standard ISO 13666) to be input;
the third zone Z3 allows a value representative of the dihedral angle Δ (associated with the frame M, as explained above) to be input;
the fourth zone Z4 allows the distance between the lateral end of the eyeglass V (or the frame M) and the temporal region RT of the head T of the wearer P, which corresponds to the width L of the incident beam (as explained above and shown in FIG. 1) to be input; and
the fifth zone Z5 allows a value (for example a coefficient) $I_{EXP}$ representative of the exposure of the wearer P to ultraviolet radiation to be input.

For example, for this fifth zone Z5 (and in this case, instead of what was described above), the icon IC is a map (of a region, a country or one or more continents) showing, via a colour code, the intensity of ultraviolet radiation for the various points on the map, and selection of this icon IC by the user leads to the display, in the first window F1, of a plurality of selectable buttons having colours respectively corresponding to those shown on the map. Thus, the user may find on the map the colour associated with his place of residence (or of use of the spectacles) and select, in the window F1, the button having the colour associated with this place on the map, so that the electronic device D" will use, by way of value $I_{EXP}$ representative of the exposure of the wearer P, the value corresponding to the selected colour.

The electronic device D" (or, as a variant, another electronic device to which the values of the parameters input by means of the electronic device D" are transmitted) may then determine the area S of the exposed portion of the back face AR depending on the values of the parameters input by means of the electronic device D".

The electronic device D" (or, as a variant, the aforementioned other electronic device) may then determine the index $I_O$ of exposure of the eye to ultraviolet radiation on the basis of the coefficient $I_{EXP}$ input in the fifth zone Z5 and of a determined coefficient $I_S$ depending on the area S, for example by multiplying the coefficient $I_{EXP}$ input in the fifth zone Z5 by the coefficient $I_S$ representative of the area S.

The obtained index $I_O$ of exposure of the eye may then be displayed to the user, for example on the screen of the electronic device D".

This index $I_O$ may be presented on a graduated scale representing the range of possible values of the index $I_O$ (with optionally a variation in the colour of the scale depending on the possible value), with an indicator level with the obtained index $I_O$, for example having a colour dependent on the value of this obtained index $I_O$ (in accordance with the variations in colour of the scale).

According to another possibility, the obtained index $I_O$ is represented on a two-dimensional graph the two dimensions of which correspond to the possible values of the coefficient representative of the area S and to the possible values of the coefficient representative of the exposure of the wearer P, respectively. The result (obtained index $I_O$) is then presented in the form of a point on the graph having for coordinates the values $I_S$ and $I_{EXP}$ obtained as indicated above. To further simplify comprehension, it is possible for this graph to feature zones of different colours each corresponding to a range of given values of the index of exposure of the eye determined depending on parameters associated with the axes of the graph (coefficient representative of the area, coefficient representative of the exposure).

The invention claimed is:

1. A method for determining an index of exposure to ultraviolet radiation of an eye of a wearer resulting from ultraviolet rays reflected from a back surface of at least one eyeglass of spectacles when worn on the head of the wearer, comprising the following steps:
 positioning the wearer in front of an image sensor;
 using the image sensor, directed facing a front of the head of the wearer along a gaze direction of the wearer, to capture an image of the head of the wearer and store said image in a memory of an electronic device;
 using a processor of the electronic device to process the captured image to determine therefrom an area of a portion of a back face of said eyeglass that is directly exposed to exterior radiation when said wearer is wearing said spectacles;
 selecting, at the electronic device, an environment frequented by the wearer; and calculating, and displaying at the electronic device, the index of exposure based on the determined area and a value representative of an exposure to ultraviolet radiation at the selected environment frequented by the wearer, in order to treat the back face of the eyeglass with an antireflective coating.

2. The method according to claim 1, wherein the processor of the electronic device obtains, from the captured image, morpho-geometric parameter values of the wearer and of a frame of said spectacles.

3. The method according to claim 1, further comprising: measuring at least one morpho-geometric parameter values of the wearer and of a frame of said spectacles.

4. The method according to claim 3, further comprising: inputting the at least one of the morpho-geometric parameter values on a user interface of the electronic device.

5. The method according to claim 1, wherein the step of determining said area comprises a step of evaluating said area from an image taken while the wearer is illuminated from behind by a coloured light.

6. The method according to claim 1, wherein the positioning of the wearer in front of the image sensor includes a sub-step of inclining the head of the wearer relative to the image sensor.

7. The method according to claim 1, further comprising: providing a projector, prior to use of the image sensor to capture the image of the head of the wearer, at a location behind the wearer, and causing the projector to illuminate a portion of the back face of at least one eyeglass of the spectacles worn by the wearer.

8. The method according to claim 7, wherein the projector illuminates the back face of at least one eyeglass with visible light.

9. The method according to claim 7, wherein the projector illuminates the back face of at least one eyeglass with ultraviolet light, and the method further includes a step of providing a revealing means to one of the back face of the at least one eyeglass of the spectacles and a frame of the spectacles.

10. A system for determining an index of exposure to ultraviolet radiation of an eye of a wearer resulting from ultraviolet rays reflected from a back surface of at least one eyeglass of spectacles when worn on the head of the wearer, comprising:
an electronic device, having at least a processor for operation of the electronic device;
an image sensor in communication with said electronic device; and
a memory in communication with the processor of the electronic device, the memory having processor code stored thereon that, upon execution by the processor, causes the electronic device to:
capture, via the image sensor, an image of the head of the wearer and store said image in the memory of an electronic device, the image sensor being operationally directed to face a front of the head of the wearer along a gaze direction of the wearer,
process the captured image to determine therefrom an area of a portion of a back face of said eyeglass that is directly exposed to exterior radiation when said wearer is wearing said spectacles,
receive input from a user to select an environment frequented by the wearer; and
calculate, and display on a display device in communication with the electronic device, the index of exposure based on the determined area and a value representative of an exposure to ultraviolet radiation at the selected environment frequented by the wearer, in order to treat the back face of the eyeglass with an antireflective coating.

11. The system according to claim 10, wherein the processing code further causes the electronic device to obtain, from the captured image, morpho-geometric parameter values of the wearer and of a frame of said spectacles.

12. The system according to claim 10, further comprising:
a device for measuring at least one morpho-geometric parameter values of the wearer and of a frame of said spectacles,
wherein the processing code further causes the electronic device to receive, by way of a user interface said at least one morpho-geometric parameter values.

13. The system according to claim 10, further comprising:
a projector, configured to illuminate a portion of the back face of at least one eyeglass of the spectacles worn by the wearer.

14. The system according to claim 10, further comprising:
a tool for inputting a piece of information on a user interface,
wherein the processing code further causes the electronic device to determine said value representative of the exposure based on said piece of information.

15. The system according to claim 10, wherein the processing code further causes the electronic device to determine the index of exposure by multiplying the determined value representative of the exposure by a coefficient dependent on the determined area.

* * * * *